United States Patent
Guerin

(10) Patent No.: US 11,359,783 B2
(45) Date of Patent: *Jun. 14, 2022

(54) LED FLAMELESS CANDLE ASSEMBLY

(71) Applicant: Aeron Lifestyle Technology, Inc., Fairfield, IA (US)

(72) Inventor: Patrick Guerin, Fairfield, IA (US)

(73) Assignee: AERON LIFESTYLE TECHNOLOGY, INC., Fairfield, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/243,645

(22) Filed: Apr. 29, 2021

(65) Prior Publication Data

US 2021/0341118 A1 Nov. 4, 2021

Related U.S. Application Data

(63) Continuation-in-part of application No. 16/865,025, filed on May 1, 2020, now Pat. No. 11,035,535.

(51) Int. Cl.
*F21S 10/04* (2006.01)
*F21V 29/60* (2015.01)
*F21V 23/00* (2015.01)
*F21Y 115/10* (2016.01)

(52) U.S. Cl.
CPC .......... *F21S 10/043* (2013.01); *F21V 23/003* (2013.01); *F21V 29/60* (2015.01); *F21Y 2115/10* (2016.08)

(58) Field of Classification Search
CPC ....... F21S 10/043; F21V 29/60; F21V 23/003
See application file for complete search history.

(56) References Cited

U.S. PATENT DOCUMENTS

| 9,360,181 B2 * | 6/2016 | Li ............................. F21S 6/001 |
| 2005/0285538 A1 * | 12/2005 | Jaworski ................. A61L 9/037 |
| | | 315/76 |

* cited by examiner

*Primary Examiner* — Thomas M Sember
(74) *Attorney, Agent, or Firm* — Zarley Law Firm P.L.C.

(57) ABSTRACT

An LED diffusing assembly having a housing, a plurality of LED lights, and an LED control circuit. Each of the plurality of LED lights has a fixed intensity. Once activated the LED control circuit activates and deactivates each LED light at different times and for different intervals to create a flickering effect.

11 Claims, 6 Drawing Sheets

LED FLAMELESS CANDLE ASSEMBLY

CROSS REFERENCE TO RELATED APPLICATION

This application claims the benefit of priority and is a continuation-in-part of pending application Ser. No. 16/865,025 filed May 1, 2020, the contents of this application is hereby incorporated by reference in its entirety.

BACKGROUND OF THE INVENTION

The present invention is directed to a flameless candle assembly and more particularly a flameless candle assembly having a simple circuit and is adapted to emit scent.

Flameless candles are well-known in the art and enhance an environment while promoting safety. Existing flameless candles use complex circuitry which adjusts the intensity as well as the duration of activation. While useful, these devices are complex and expensive to manufacture. Accordingly, a need exists in the art for a device that addresses these deficiencies.

An objective of the present invention is to provide an LED flameless candle assembly having a simple control circuit.

Another objective of the present invention is to provide an LED flameless candle assembly that is less expensive to manufacture.

These and other objectives will be apparent to one skilled in the art based upon the following written description, claims, and drawings.

SUMMARY OF THE INVENTION

An LED flameless candle assembly has a housing, a plurality of LED lights, and an LED control circuit. The housing has a base removably connected to a body to form a chamber. Disposed within the chamber is the LED control circuit, a power supply, and a fan.

The body of the housing has a partially open top wall. Centrally located on the top wall and extending vertically away from the body is a flameless candle. The flameless candle has a shaft section connected to a semi-translucent section preferably having the shape of a flame. The plurality of LED lights is disposed in the semi-translucent section and are connected to the LED circuit control through the shaft. A scent diffusing disk fits around the shaft section of the flameless candle and engages the partially open top wall of the housing.

Each of the plurality of LED lights has a fixed intensity. The LED circuit control activates each LED light at different times and for different durations to create a flickering effect.

DETAILED DESCRIPTION OF THE PREFERRED EMBODIMENTS

Figure 1:
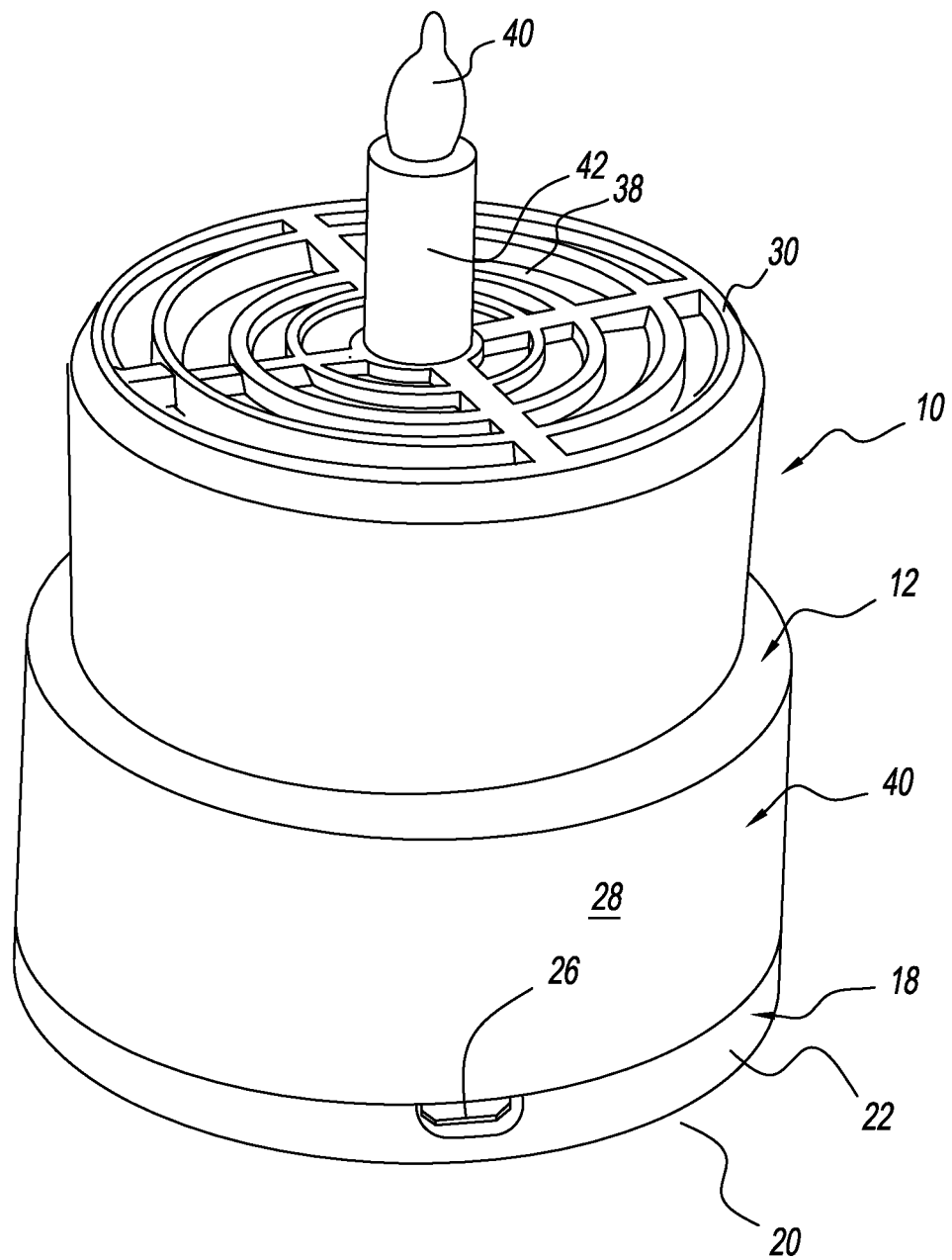
FIG. 1 is a perspective view of an LED flameless candle assembly.
Figure 2:
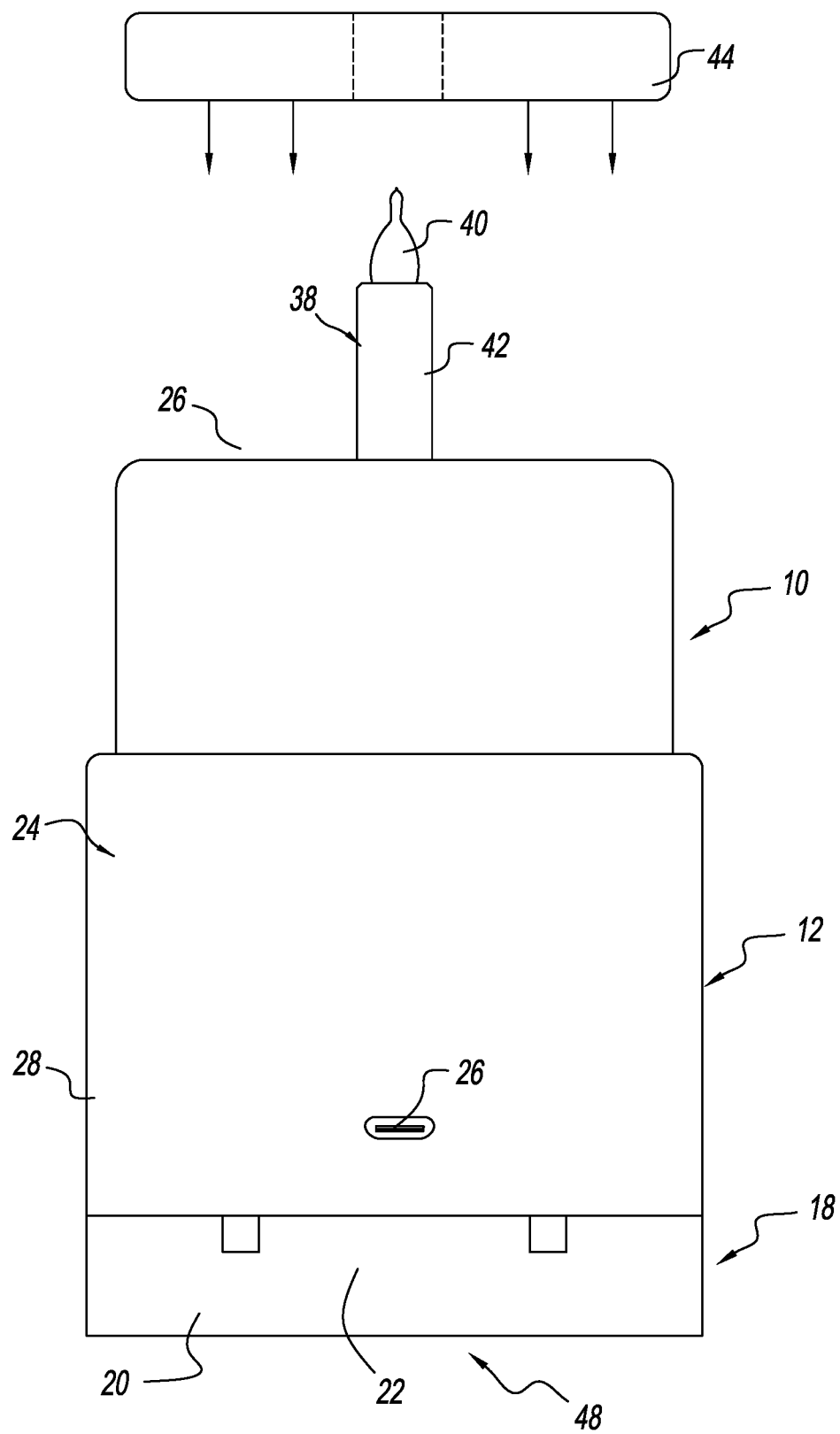
FIG. 2 is a side view of an LED flameless candle assembly.
Figure 3:
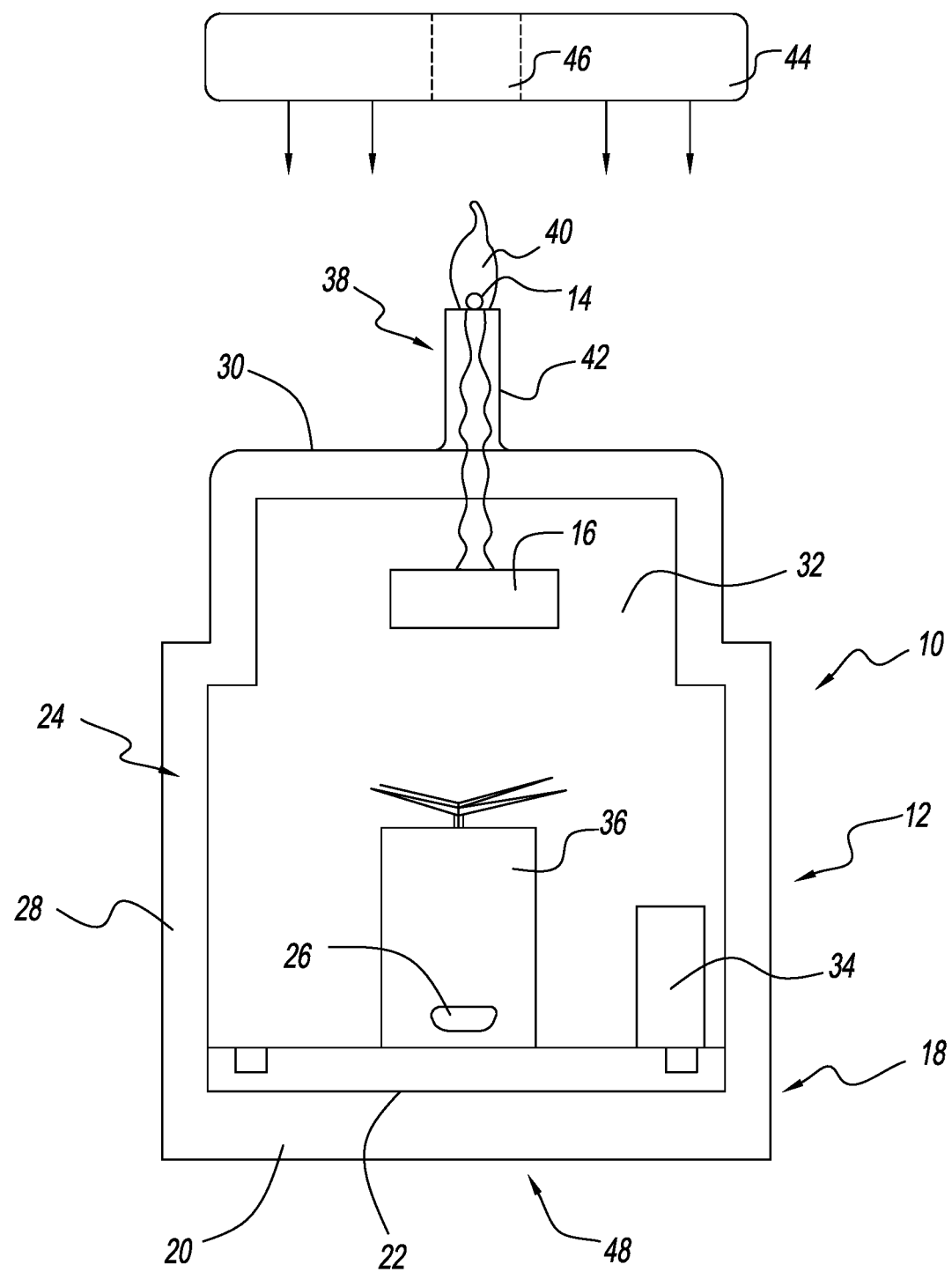
FIG. 3 is a side sectional view of an LED flameless candle assembly.
Figure 4:
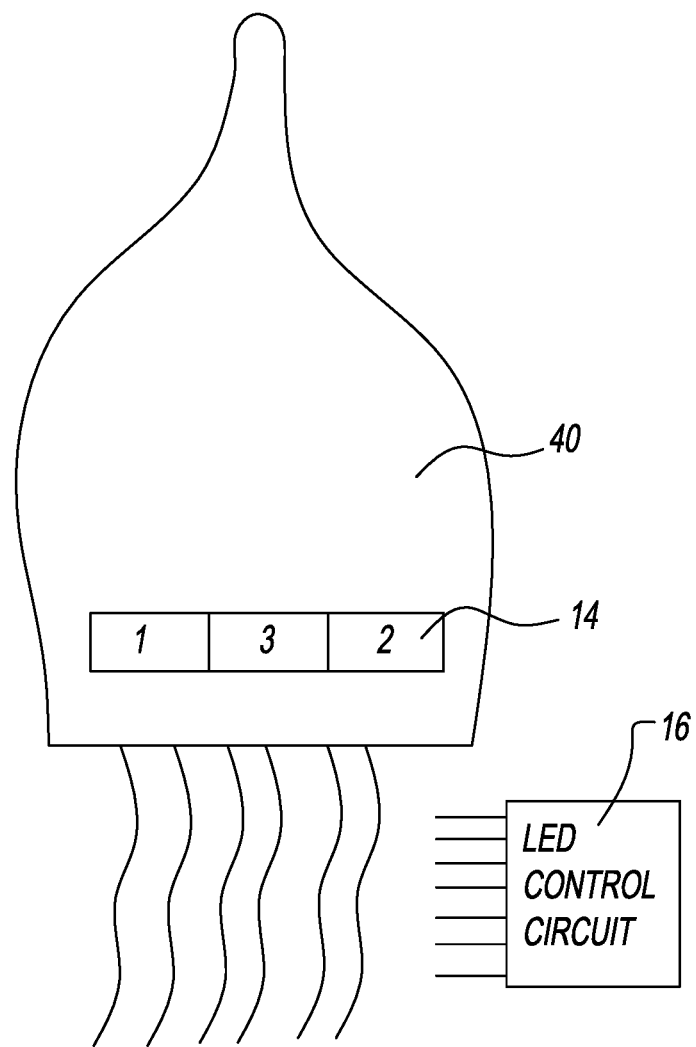
FIG. 4 is a partial view of a semi-translucent section of a flameless candle.
Figure 5:
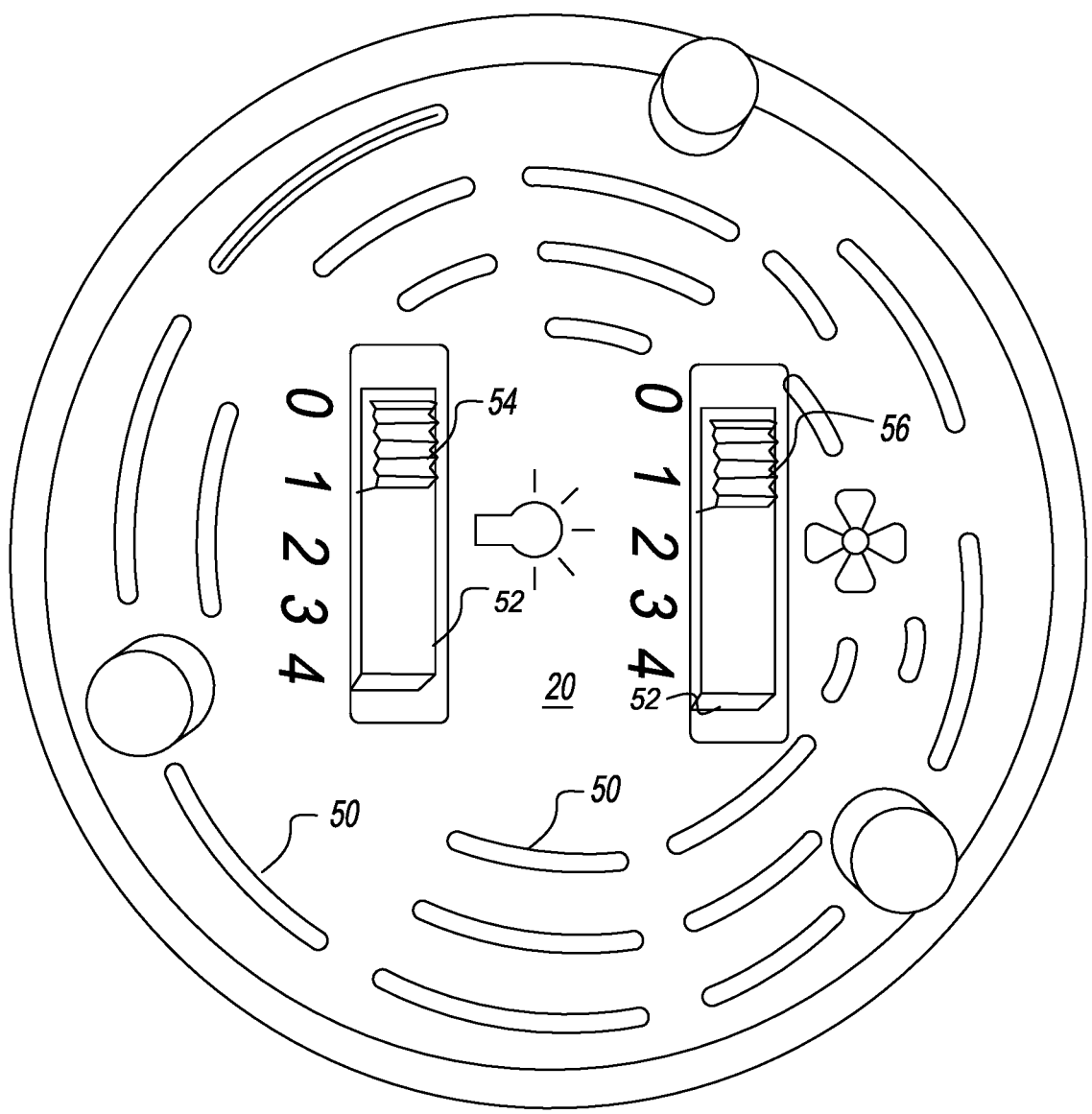
FIG. 5 is a bottom view of an LED flameless candle.
Figure 6:
FIG. 6 is a perspective view of a decorative sleeve of an LED flameless candle.

Referring to the Figures, an LED flameless candle diffuser 10 includes a housing 12, a plurality of LED lights 14, and an LED control circuit 16. The housing 12 is of any size, shape, and structure.

In the example shown, the housing 12 has a base 18 having a partially open bottom wall 20 and a side wall 22 that are removably connected to a body 24 of the housing 12 and a power source, such as a USB 26 disposed in the side wall 22. The body 24 of the housing 12 has a side wall 28 and a partially open top wall 30 that form a chamber 32. Disposed within the chamber 32 is the LED control circuit 16, a power source 34 such as replaceable or rechargeable batteries, and a fan 36.

Centrally located on the partially open top wall 30 and extending vertically away from the top wall 30 is a flameless candle 38 having a semi-translucent section 40 connected to a shaft section 42. Preferably, the semi-translucent section 40 has a flame-like shape. Disposed within the semi-translucent section 40 are the plurality of LED lights 14. The LED lights 14 are connected to the LED control circuit 16 through the shaft section 42. Each of the plurality of LED lights 14 emit a different fixed light intensity. For example, a first LED may have 100% light intensity, a second LED may have 50% light intensity, and a third LED may have 10% light intensity.

Fitted down and around the shaft section 42, to engage the partially open top wall 30 of the housing 12, is a scent emitting disk 44. The disk 44 is of any size, shape, and structure and preferably is circular having a central opening 46 adapted to receive the shaft section 42 of the housing 12. A decorative sleeve 48, having a diameter greater than the diameter of the body 24 and is adapted to fit over the diffuser 10. The partially open bottom wall 20 and top wall 30 have vents 50 which permit air flow through the diffuser 10. The bottom wall 20 also has openings 52 for a light switch 54 and a fan switch 56 that are connected to the control circuit 16 to control the operation of the lights 14 and fan 36. Both switches 54 and 56 can be set at various intervals of time.

In operation, the diffuser 10 is activated by engaging a switch 54 and/or 56 that extends through the housing 12 and is connected to the power source 34. Once activated the power is supplied to the LED control circuit 16 which in turn activates the LED lights 14 and/or turns on the fan 36. Each of the plurality of LED lights having fixed intensities are randomly activated with the time for activated intervals and deactivated intervals varied. As a result, using the example of a system with three LED lights, at any given time, one, two, or three lights will be activated providing a flickering effect through the semi-translucent section 40. The circuit control 16 also activated the fan 36. Once activated, air flows from the bottom wall 20 toward the partially open top wall 30 of the housing from the fan 36 through the scent emitting disk 44 where scent is dispersed.

Accordingly, an LED flameless candle diffuser 10 has been disclosed, that at the very least meets all the stated objectives. From the above discussion and accompanying figures and claims it will be appreciated that the LED flameless candle diffuser 10 offers many advantages over the prior art. It will be appreciated further by those skilled in the art that other various modifications could be made to the device without parting from the spirit and scope of this invention. All such modifications and changes fall within the scope of the claims and are intended to be covered thereby. It should be understood that the examples and embodiments described herein are for illustrative purposes only and that various modifications or changes in the light thereof will be suggested to persons skilled in the art and are to be included in the spirit and purview of this application.

What is claimed is:

1. An LED flameless candle assembly, comprising:
   a housing having a base removably connected to a body;
   the base having a side wall and a top wall and a partially open bottom wall;
   the body having a side wall and a partially open top wall through which a flameless candle extends vertically, wherein the body and base form a chamber;
   a plurality of LED lights;
   an LED control circuit disposed within the chamber of the housing and connected to the plurality of LED lights; and
   wherein the LED control circuit is configured to activate and deactivate the plurality of LED lights at varying intervals to create a flickering effect;
   wherein each light of the plurality of lights has a different fixed intensity.

2. The assembly of claim 1 further comprising the top wall of the housing having a first plurality of vents and the bottom wall of the base having a second plurality of vents.

3. The assembly of claim 1 wherein the bottom is partially open.

4. The assembly of claim 1 wherein a scent emitting disk is fitted around the flameless candle.

5. The assembly of claim 1 wherein a fan is disposed within the housing.

6. The assembly of claim 1 where a sleeve fits over the housing.

7. An LED flameless candle assembly, comprising:
   a housing having a base removably connected to a body;
   a plurality of LED lights;
   an LED control circuit disposed within the housing and connected to the plurality of LED lights;
   wherein the LED control circuit activates and deactivates the plurality of LED lights at varying intervals to create a flickering effect; and
   a bottom wall of the base having a light switch and a fan switch, wherein the light switch is configured to operate the plurality of LED lights and the fan switch is configured to operate a fan disposed within the housing, including to set a plurality of time intervals for operation of the fan.

8. The assembly of claim 7 wherein the light switch is configured to set a plurality of time intervals for operations of the plurality of lights.

9. The assembly of claim 7 wherein each light of the plurality of LED lights has a different fixed intensity.

10. An LED flameless candle assembly, comprising:
    a housing;
    a plurality of LED lights;
    an LED control circuit disposed within the housing and connected to the plurality of LED lights;
    wherein the LED control circuit activates and deactivates the plurality of LED lights at varying intervals to create a flickering effect;
    the housing having a base removably connected to a body;
    the base having a side wall and a partially open top wall and a partially open bottom wall;
    the body having a top wall and a side wall; and
    the top wall of the housing having a first plurality of vents and the partially open bottom wall of the base having a second plurality of vents.

11. The assembly of claim 10 wherein each light of the plurality of LED lights has a different fixed intensity.

* * * * *